(12) United States Patent
Friedrich et al.

(10) Patent No.: US 9,816,909 B2
(45) Date of Patent: Nov. 14, 2017

(54) CONTACT ANGLE MEASUREMENT APPARATUS

(71) Applicant: KRUESS GMBH, Wissenschaftliche Laborgeraete, Hamburg (DE)

(72) Inventors: Bernd Friedrich, Hasloh (DE); Florian Weser, Hamburg (DE); Carsten Scheithauer, Hamburg (DE)

(73) Assignee: KRUESS GMBH, WISSENSCHAFTLICHE LABORGERAETE, Hamburg (DE)

( * ) Notice: Subject to any disclaimer, the term of this patent is extended or adjusted under 35 U.S.C. 154(b) by 237 days.

(21) Appl. No.: 14/604,965

(22) Filed: Jan. 26, 2015

(65) Prior Publication Data

US 2015/0211973 A1  Jul. 30, 2015

(30) Foreign Application Priority Data

Jan. 24, 2014 (EP) .................................... 14152563

(51) Int. Cl.
*G01N 13/02* (2006.01)

(52) U.S. Cl.
CPC ..... *G01N 13/02* (2013.01); *G01N 2013/0208* (2013.01)

(58) Field of Classification Search
CPC .................. G01N 13/02; G01N 13/00; G01N 2013/0208; G01F 1/00; G01F 1/25; G01F 1/0007

(Continued)

(56) References Cited

U.S. PATENT DOCUMENTS

| 4,697,451 A | * | 10/1987 | Matteson | ............... | G01N 13/02 |
| | | | | | 324/71.4 |
| 5,479,816 A | * | 1/1996 | Richou | .................. | G01N 13/02 |
| | | | | | 73/64.48 |

(Continued)

FOREIGN PATENT DOCUMENTS

| DE | 19754765 C1 | 1/1999 |
| DE | 197 54 765 C1 | 7/1999 |

(Continued)

OTHER PUBLICATIONS

Yuehua Yuan and T. Randall Lee, "Contact Angle and Welling Properties" Springer Series in Surface Sciences 51, DOI 10. © Springer-Verlag Berlin Heidelberg 2013.

(Continued)

*Primary Examiner* — Peter Macchiarolo
*Assistant Examiner* — Hoang Nguyen
(74) *Attorney, Agent, or Firm* — Stuart H. Mayer; Mayer & Williams PC

(57) ABSTRACT

A contact angle measurement apparatus includes a liquid reservoir arrangement, a drop dosing device in fluid communication with the liquid reservoir arrangement and adapted for applying a liquid drop onto a sample surface, an illuminating device for illuminating each drop applied by the drop dosing device and disposed on the surface from a first side, and an image recording device for recording an image of each applied drop disposed on the surface. A liquid pressurizing system is adapted to pressurize liquid from the liquid reservoir arrangement, and a controller connected to the valve of each drop dosing device and to the liquid pressurizing system, which controls the operation of the liquid pressurizing system and, for each drop dosing device, opening and closing of the respective valve to apply a drop (Continued)

of the respective liquid from the respective liquid line to the surface in a jet of pressurized liquid.

15 Claims, 3 Drawing Sheets

(58) Field of Classification Search
USPC .............................................. 73/64.48, 64.52
See application file for complete search history.

(56) References Cited

U.S. PATENT DOCUMENTS

| | | | | |
|---|---|---|---|---|
| 5,894,036 | A * | 4/1999 | Tylko | B41M 3/00 |
| | | | | 118/696 |
| 7,952,698 | B2 * | 5/2011 | Friedrich | G01N 13/02 |
| | | | | 356/138 |
| 9,186,667 | B2 * | 11/2015 | Ikushima | B01L 3/0265 |
| 2003/0097871 | A1 * | 5/2003 | Mansky | B01J 19/0046 |
| | | | | 73/64.49 |
| 2006/0292304 | A1 | 12/2006 | Tisone | |
| 2009/0320568 | A1 * | 12/2009 | Desie | G01N 11/06 |
| | | | | 73/54.07 |
| 2010/0024529 | A1 * | 2/2010 | Dillingham | G01N 13/02 |
| | | | | 73/64.52 |
| 2011/0073200 | A1 * | 3/2011 | Overvaag | G05D 16/04 |
| | | | | 137/528 |
| 2015/0072370 | A1 * | 3/2015 | Tanaka | G01N 13/00 |
| | | | | 435/29 |

FOREIGN PATENT DOCUMENTS

| | | | |
|---|---|---|---|
| DE | 19754765 | * | 7/1999 |
| DE | 10022503 A1 | | 5/2001 |
| EP | 0919801 A | | 10/1998 |
| EP | 0919801 A1 | | 6/1999 |
| EP | 1650544 B1 | | 12/2008 |
| EP | 2555000 A1 | | 3/2011 |
| JP | 54126295 | | 9/1979 |
| JP | 62-182665 | | 8/1987 |
| JP | 11-230886 | | 8/1999 |
| JP | 2013-192544 | * | 9/2013 |
| WO | 03/072258 A1 | | 9/2003 |

OTHER PUBLICATIONS

Larousse "Dictionary of Science and Technology", p. 598, copyright 1995.

* cited by examiner

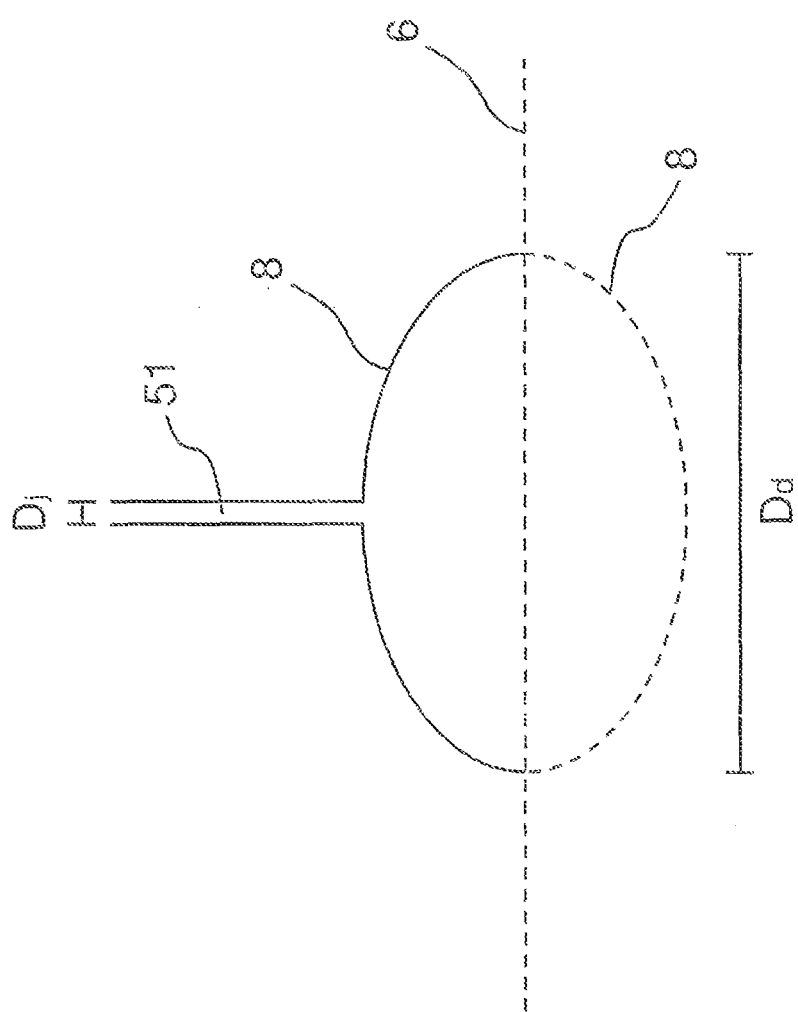

CONTACT ANGLE MEASUREMENT APPARATUS

BACKGROUND OF THE INVENTION

The present application relates to a contact angle measurement apparatus for measuring a contact angle between a surface of a sample body and at least one drop of sample liquid disposed on the surface, the apparatus comprising a liquid reservoir arrangement for storing at least one liquid, at least one drop dosing device in fluid communication with the liquid reservoir arrangement and adapted and arranged for applying a drop of a liquid stored in the liquid reservoir arrangement onto a surface of a sample body, an illuminating device adapted and arranged for illuminating each drop applied by the at least one drop dosing device and disposed on the surface from a first side of the at least one drop, and an image recording device adapted and arranged for recording an image of at least a transition region between the surface and each drop applied by the at least one drop dosing device and disposed on the surface in side view from a second side of the drop opposite the first side.

The wettability of liquids on surfaces of solids is of great importance in many fields of technology, such as in the field of industrial production. For example, processes such as coating, painting, cleaning, printing, hydrophobic or hydrophilic coating, bonding, dispersion, etc. are influenced in a decisive manner by the wettability.

For a particular pair of solid and liquid the wettability is determined by, amongst others, the surface free energy of the solid and the surface tension of the liquid. In view of the fact that, following application of the liquid onto a surface of the solid, these parameters also determine the angle between the surface of the liquid and the surface of the solid at the point at which the surface of the liquid meets the surface of the solid, a measurement of this so-called contact angle can be used as a measure of the wettability. On this basis methods are known for characterizing surfaces of solid bodies with respect to their wettability properties by applying one or more drops of liquids having known properties (in particular known surface tensions) and serving as "sensors" onto a surface of interest and measuring the corresponding contact angle or angles. When using two or more different liquids having a different degree of polarity, it is further possible to derive the surface free energy from the measured contact angles of drops of the different liquids.

DE 197 54 765 C1 discloses a contact angle measurement apparatus which is adapted for carrying out methods of these types. It includes a syringe type drop dosing device adapted for metering a drop of liquid onto a surface of a solid sample body, an illuminating device adapted and arranged for illuminating the drop from a first side and a camera for recording a shadow image of the drop from a second side opposite the first side. Further, an image processing device is provided which is adapted to carry out a recognition of the contour of the drop and of the surface of the solid in the image recorded by the camera and to subsequently determine the contact angle based on the recognized contour and surface.

A syringe type drop dosing device, such as used in DE 197 54 765 C1, is operated by moving it close to a surface, onto which a drop is to be applied, and transferring a drop located at the tip of a needle of the drop dosing device from the needle to the surface. This has the disadvantage that for surfaces located at different positions the needle has to be moved to different positions and care has to be taken that the tip of the needle does not contact the surface at issue. Moreover, the transfer of the drop from the tip of the needle to the surface is a complicated process. Therefore, the entire drop dosing process is relatively slow.

Further, in case the surface free energy is to be determined, either two or more drops of different liquids have to be applied to the surface one after the other using the same drop dosing device, or two or more of the syringe type drop dosing devices have to be provided next to each other and have to be connected to liquid reservoirs storing the different liquids or provided with the different liquids in a different manner, such as, e.g., by manually drawing the liquids into the piston chambers of the drop dosing devices. While the first option has the disadvantage that the speed of the measuring process is even further decreased, also because of the need to avoid any contamination of the liquids among each other, the second option has to take into consideration that the syringe type drop dosing devices are rather bulky. Consequently, it is difficult to place the drops sufficiently close to each other to be able to record them in a single image when using a conventional camera.

SUMMARY OF THE INVENTION

It is an object of the present invention to provide a contact angle measurement apparatus which facilitates safe use of the apparatus and allows for an increased speed of measurement, and which overcomes the above disadvantages.

This object is achieved by a contact angle measurement apparatus according to claim 1. Advantageous embodiments of the apparatus are the subject-matter of the respective dependent claims.

The contact angle measurement apparatus is adapted to measure a contact angle between a surface of a solid sample body and one or more drops of sample liquid disposed on the surface. In case of two or more drops, which may be drops disposed on the surface next to each other at the same time or drops disposed on the surface at different points in time, the contact angle is measured for each drop of interest.

The apparatus comprises a liquid reservoir arrangement for storing one, two or more liquids. It has at least one liquid reservoir. In case two or more liquids are to be used, the liquid reservoir arrangement preferably includes a corresponding number of separate liquid reservoirs, each adapted for storing a different one of the liquids. In operation, liquid or liquids to be used for forming drops on a surface of a sample body is or are stored in the liquid reservoir arrangement, more particularly in a liquid reservoir or liquid reservoirs of the liquid reservoir arrangement.

The apparatus also includes one, two or more drop dosing device, which are each in fluid communication with the liquid reservoir arrangement, more particularly with at least one liquid reservoir of the liquid reservoir arrangement. Each of these drop dosing devices is adapted and arranged for applying a drop of a liquid stored in the liquid reservoir arrangement onto a surface of a sample body. This process is carried out by metering the drop, which may advantageously be effected such that it has a defined drop volume. In case two or more drop dosing devices are provided, they may be coupled to the liquid reservoir arrangement such that they apply the same liquid to different locations on the surface, e.g. in order to determine variations of the surface properties. However, as will be explained in more detail further below, it is preferred for two or more drop dosing devices being coupled to different liquid reservoirs of the liquid reservoir arrangement storing different liquids.

Moreover, the apparatus comprises an illuminating device and an image recording device. The illuminating device is adapted and arranged for illuminating any drop applied by the drop dosing device or drop dosing devices and disposed on the surface from a first side of the respective drop, and the image recording device is adapted and arranged for recording an image of any such drop or of at least a transition region between the surface and any such drop in side view from a second side of the drop opposite the first side. Thus, the relative arrangement of the illuminating device and the image recording device is such that images of drops can be recorded in a back-lit lighting arrangement to obtain shadow images of the drops. It is to be noted that a separate image may be recorded for each of the above drops, or a single image may be recorded for a plurality of the above drops or all of the above drops.

Each of the drop dosing devices comprises a liquid line or conduit, which may include a cannula or needle and/or a tube and which comprises an outlet and a valve adapted for selectively blocking and allowing flow of liquid through the liquid line. The outlet may be provided by, e.g., a nozzle or by a part of the valve. The liquid line is adapted and arranged to guide a liquid stored in the liquid reservoir arrangement towards the outlet and out of the outlet onto the surface. Thus, the liquid line is in direct or indirect fluid communication with at least one associated liquid reservoir, which forms part of the liquid reservoir arrangement.

The contact angle measurement apparatus further comprises a liquid pressurizing system, on which the drop dosing devices rely for driving liquid out of their respective outlet onto the surface, and which is adapted to pressurize liquid from the liquid reservoir arrangement. The liquid pressurizing system may preferably include or be a compressed gas system comprising a source of pressurized gas which is adapted to provide pressurized gas at a defined pressure. Such a pressurized gas system is adapted to pressurize liquid from or stored in the liquid reservoir arrangement using the pressurized gas. In this regard, a part of an interior space of any liquid reservoir contained in the liquid reservoir arrangement may be adapted to hold liquid, and another part of the interior space, separated from the first part by a media separation means, may serve as pressure reservoir to which the pressurized gas is supplied. For distribution of the pressurized gas, the gas system preferably includes a pressurized air manifold. The gas may preferably be air; in that case the pressurized gas system is an air system.

Further, the contact angle measurement apparatus comprises a controller which is connected both to the valve of each of the drop dosing devices and to the liquid pressurizing system. The controller is adapted to control and preferably automatically control the operation of the liquid pressurizing system, in particular the pressure with or to which the liquid is pressurized, and, for each of the drop dosing devices, opening and closing of the respective valve to apply a drop of the respective liquid, which may advantageously have a defined drop volume, from the outlet of the respective liquid line to the surface in a jet of pressurized liquid. This jet, which is driven by the pressure provided by the liquid pressurizing system, such as by pressurized gas from a compressed gas system, is preferably a continuous stream, but—depending on the properties of the liquid at issue and the flow parameters—may in principle also include or consist of a plurality of droplets.

The controller may advantageously be an electronic component, such as a microcontroller, which may be integrated into a common housing with some or all of the remaining components of the apparatus. However, it is, e.g., also possible to provide the controller as a separate computing device, such as a suitably programmed computer or PC, connected to the remainder of the apparatus and not integrated into a common housing with other components of the apparatus.

In any case, for each of the drop dosing devices the controller and the valve are adapted such that the jet applies the liquid to the surface with a flow rate of 45 µl/s or less, preferably about 40 µl/s or less, more preferably about 35 µl/s or less, even more preferably about 30 µl/s or less, and most preferably 25 µl/s or about 25 µl/s. However, the flow rate may also be 25 µl/s or less. Further, it is preferred if the flow rate is at least 0.05 µl/s, preferably at least 0.1 µl/s, more preferably at least 0.15 µl/s, even more preferably at least 0.2 µl/s and most preferably at least 0.25 µl/s. In any case, the flow rate may be controlled by the controller by, e.g., controlling and adjusting the degree of opening of the valve and/or the pressure provided by the liquid pressurizing system (e.g. the defined pressure of pressurized gas provided by a compressed gas system). It has been found that the above flow rate is sufficiently low to enable precise measurements.

Due to the above construction, for the application of drops to the surface it is not necessary to move a needle close to the surface and to transfer drops from the tip of the needle to the surface. Rather, liquid for forming drops can be ejected from the outlets of the drop dosing devices and move over a relatively large space between the outlets and the surface. In this regard, it has been surprisingly found that when applying a drop by means of a jet of liquid fulfilling the above flow rate condition, it is nevertheless advantageously possible to distribute the total kinetic energy of the liquid transferred to the surface over a sufficiently long period of time in order to maintain the kinetic energy at each instant sufficiently low to enable reproducible formation of drops exhibiting equilibrium contact angle. Advantageously, the metering of drops in this manner does not require taking care not to damage the surface or a needle when moving the needle close to the surface, and avoids problems with drops adhering to the tip of a needle and with adjusting the transfer position of a needle for different surface positions. Overall, a much faster drop formation is possible as compared to the prior art apparatuses. Moreover, it is easily possible without taking additional measures to utilize liquids of different viscosities. In particular, liquids having a particular high viscosity can be used and merely require an increase of the pressure with which they are pressurized. Also, as compared to prior art apparatuses the apparatus of the present invention is relatively insensitive to contamination and is relatively simple to clean. For example, the nozzles and valves can be cleaned in an ultrasonic cleaning device.

In an advantageous embodiment the entire apparatus may be constructed as a mobile apparatus. It is easily possible to select suitable components for the construction of the apparatus, which components are of sufficiently small dimensions. However, depending on the application at issue, the entire apparatus or at least parts of the apparatus may also be constructed to be stationary, i.e. non-mobile.

It is to be noted that the apparatus may be used both for planar and for curved surfaces, wherein the construction of the apparatus determines the allowable maximum curvature in that it must be possible to record shadow images of the drops in the manner described above. The apparatus may include a support structure by means of which it can be supported on the surface on which the measurement is to be carried out and/or by means of which it can be suspended above the surface. Of course, it is also possible that the apparatus is held in its measurement position above or on the surface by a suitable external holding means. Such support structure or holding means may be constructed to be adjustable in order to allow for adaptability to surfaces of different shapes. In addition or in the alternative, the illuminating device and/or the image recording device may be constructed to have adjustable positions in order to allow for such adaptability.

In a preferred embodiment, for each of the drop dosing devices the liquid line and the valve are configured such that, when applying a drop having a contact angle of 90°, i.e. a "half drop", the ratio of the diameter of the jet to the diameter of the drop is 0.2 or less, preferably 0.15 or less, more preferably 0.1 or less, and most preferably 0.06 or about 0.06. Further, it is preferred if the ratio is at least 0.01, i.e. if the ratio is in a range of 0.01 to 0.2, preferably 0.01 to 0.15 and more preferably 0.01 to 0.1. In this regard, it has been surprisingly found that when applying a drop by means of a thin jet of liquid fulfilling the above diameter condition, it is nevertheless advantageously possible to further improve the distribution of the total kinetic energy of the liquid transferred to the surface over a long period of time in order to maintain the kinetic energy at each instant low to enable reproducible formation of drops exhibiting equilibrium contact angles. In effect, the metering of drops in this manner is comparable to the metering with a thin needle.

In a preferred embodiment, the controller is adapted to adjust, for each of the drop dosing devices, the drop volume by adjusting the time interval during which the respective valve is opened, the degree of opening of the respective valve and/or the pressure provided by the liquid pressurizing system (e.g. the defined pressure of pressurized gas provided by a compressed gas system).

In a preferred embodiment, in which the liquid pressurizing system includes or is a compressed gas system, the source of pressurized gas comprises a pump, a pressure regulator, a pressure sensor and a pressure relief valve. The pump is adapted and arranged for pressurizing gas. The pressure regulator may be provided as a separate component, but it preferred that the pressure regulator is implemented by the controller, i.e. that controller is operable as the pressure regulator by including a suitable hardware component and/or software component adapted to carry out this function. In any case, the pressure regulator is adapted and arranged to regulate the pressure of gas pressurized by the pump. The pressure sensor is connected to the pressure regulator (i.e., in case the pressure regulator is implemented by the controller, the pressure sensor is connected to the controller) and is adapted and arranged to sense the pressure of the pressurized gas regulated by the pressure regulator. It should be noted that in addition or instead it is also possible that the pressure sensor is adapted and arranged to sense the pressure of a liquid from or stored in the liquid reservoir arrangement and pressurized by the pressurized gas. In any case, the pressure sensor is operable to provide a corresponding sensing signal to the controller enabling the controller to determine the sensed pressure. The pressure relief valve is connected to the pressure regulator (i.e., in case the pressure regulator is implemented by the controller, the pressure relief valve is connected to the controller) and is adapted and arranged to selectively relief pressurized gas from the portion of the source of pressurized gas covered by the regulation by the pressure regulator. The pressure regulator is adapted to control the pump and the pressure relief valve to automatically adjust the pressure of the pressurized gas based on the pressure sensed by the at least one sensor and the defined pressure in order to provide the pressurized gas with the defined pressure.

In a preferred embodiment, each of the drop dosing devices is arranged to apply drops of liquid in a field of view of the image recording device and/or in a region illuminated by the illuminating device. Consequently, the image recording device, the sample body and/or the illuminating device do not have to be moved after application of a drop, thereby decreasing the time necessary for recording an image of the drop after its application.

In this embodiment, but also in general, it is preferred if the drop dosing device or drop dosing devices, the illuminating device and the image recording device are integrated into a movable measurement head. This provides for a particularly compact and easy to use configuration, and is made possible by the specific construction of the drop dosing devices, which are considerably less bulky than the syringe type drop dosing devices known from the prior art.

The image recording device may be a camera or a device including a light-sensitive sensor, such as, e.g., a CCD image sensor or a CMOS image sensor. Thus, the image recording device may be, e.g., a CCD or CMOS camera.

In a preferred embodiment, the contact angle measurement apparatus further comprises a processing device, which is connected to or forms part of the image recording device and which is adapted for carrying out a contour recognition of any drops present in images recorded by the image recording device and determining for each of these drops a contact angle from the recognized contour. The contour recognition may be based, e.g., on a grey-scale analysis of the image and then fitting a geometrical model describing the drop shape to the image in order to determine the contour.

In a preferred embodiment, the contact angle measurement apparatus comprises two of the drop dosing devices, wherein the outlets of the two drop dosing devices are arranged such that two drops can be applied to the surface next to each other, e.g. at a distance between the centers of the drops of about 6 mm. The drops may preferably have a diameter of 4 mm or less and preferably 2 mm or less when applied to have a contact angle of 90°. In this embodiment it is further preferred if the liquid reservoir arrangement comprises two liquid reservoirs for storing two different liquids, and the liquid line of each of the two drop dosing devices is in fluid communication with a different one of the two liquid reservoirs, thereby allowing for fast measurement of the surface free energy. Alternatively or in addition it is also preferred if the controller is adapted to control the valves of the two drop dosing devices in such a manner that the two drop dosing devices simultaneously apply two drops to the surface next to each other. In any case, it is preferred if the image recording device is adapted to record an image of the two drops simultaneously, thereby decreasing the overall measurement time.

In a preferred embodiment, the contact angle measurement apparatus further comprises an actuation means, such as a button or switch, for actuation by an operator and connected to the controller. The controller is adapted to detect actuation of the actuation means and, upon detecting actuation, to automatically control the drop dosing device or drop dosing devices to apply a respective drop of liquid to the surface, the illuminating device to illuminate each such drop, and the image recording device to record an image of each such drop illuminated by the illuminating device. Thus, a "one click solution" is provided which greatly simplifies use of the apparatus. In case the apparatus includes a processing device of the above configuration for carrying out contour recognition and contact angle determination, the one click solution advantageously also comprises automatically controlling the processing device by the controller to determine the contact angle for each of the drops. Consequently, it is only necessary for the operator to move the contact angle measurement apparatus into a suitable position above the surface and to actuate the actuation means, and subsequently the apparatus is operating autonomously until the desired measurement results are provided. Further, in case of a configuration described above employing two drop dosing devices, it is preferred if the controller is adapted to automatically control, upon detecting actuation of the actuation means, each of the two drop dosing devices such that two drops are applied to the surface next to each other.

BRIEF DESCRIPTION OF THE DRAWINGS

In the following an exemplary embodiment of the display device will be explained in more detail with reference to the drawings.

FIG. 3 shows a schematic representation of the formation of a drop by one of the drop dosing devices of FIG. 2.

DETAILED DESCRIPTION OF THE INVENTION

Figure 1:
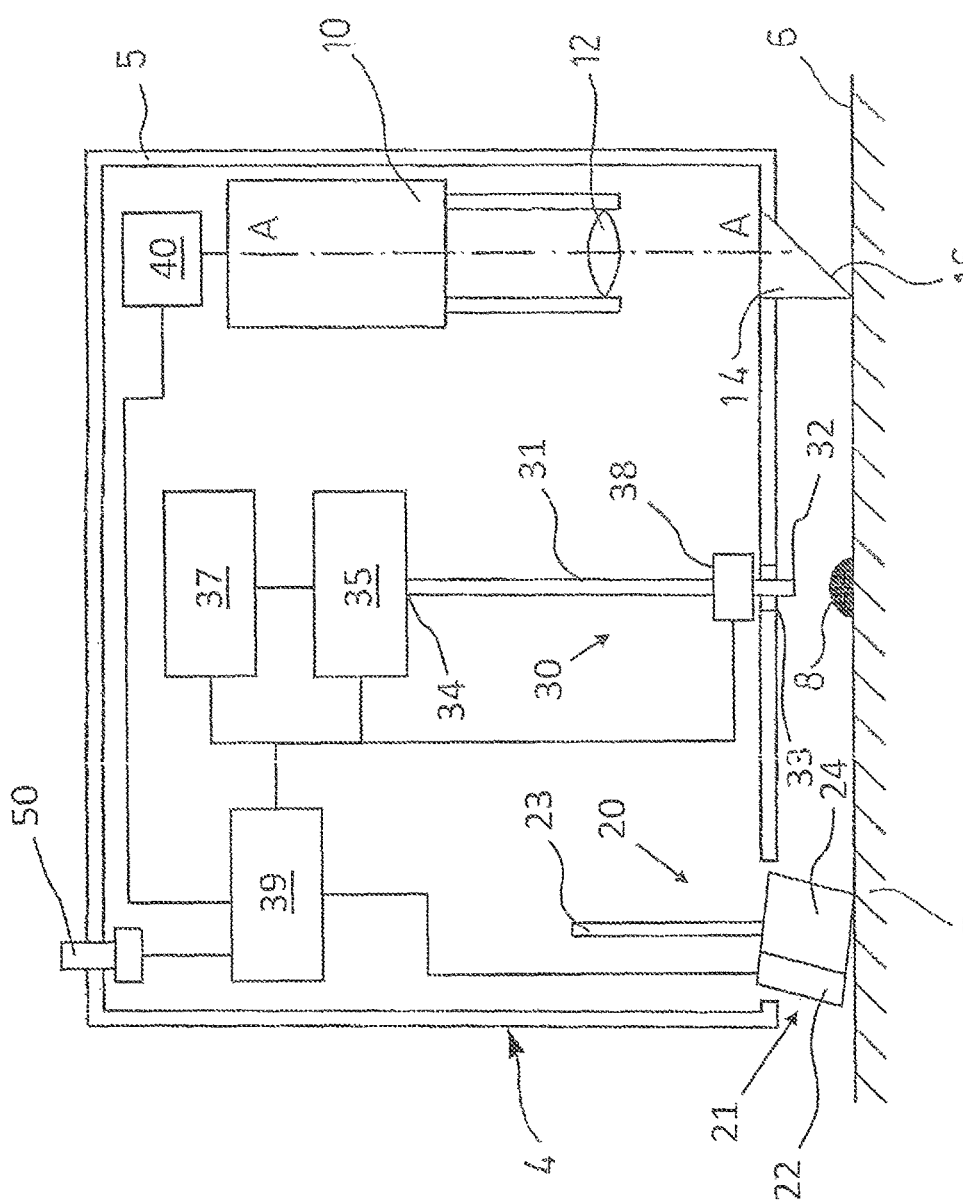
FIG. 1 shows a schematic sectional side view of the contact angle measurement apparatus according to an embodiment of the present invention.

The contact angle measurement apparatus 4 shown in FIG. 1 in a schematic sectional side view is illustrated in its measurement position closely above the surface 6 of a solid sample body 7, which surface 6 is preferably oriented horizontally. It can be seen that a drop 8 is disposed on the surface 6. The contact angle measurement apparatus 4 is operable to determine the angle between a tangent of the contour of the drop 8 and the surface 6 of the sample body 7 at a point where the contour and the surface 6 meet, i.e. which is common to the surface 6 and the contour. In the illustration of FIG. 1 the tangent extends in the plane of the Figure. For a correct fitting of the tangent to the contour of the drop 8 it is necessary that the drop 8 or at least a transition region between the drop 8 and the surface 6 of the sample body 7 is imaged in side view, which in the case of FIG. 1 is done by viewing the drop 8 from the right.

For this purpose, the apparatus 4 comprises inside a housing 5 a camera 10. The optical axis A-A of the camera 10 extends perpendicularly to the surface 6 of the sample body 7. However, when suitably adapting the imaging beam path, it is also possible to provide an angle between the optical axis A-A and the surface 6 different from 90°. The camera 10 includes a lens 12, which is preferably focusable automatically.

Projecting from the bottom side of the housing 5 is a total-reflection prism 14 which serves as a deflection means for the imaging beam path of the camera 10. The prism 14 enables recording an image of the drop 8 by the camera 10 in side view parallel or essentially parallel to the surface 6. Total reflection is occurring at the side face 16 of the prism 14.

The apparatus 4 further comprises an illuminating device 20 which is disposed opposite the camera 10 on the other side of the drop 8. The illuminating device 20 includes an illuminating unit 21 and a spring suspension arrangement 23 mounted inside the housing 5 and carrying the illuminating unit 21 in such a manner that the illuminating unit 21 projects or may project from the bottom side of the housing 5 and—in operation, i.e. in the measurement position illustrated in FIG. 1—can be elastically pressed against the surface 6. The spring suspension arrangement 23 may preferably comprise one or more leaf springs (not shown) which are arranged and constructed to allow for guided movement of the illuminating unit 21 in a direction parallel to the optical axis A-A. In other words, the leaf spring or leaf springs provide a substantially higher resistance against movement perpendicularly to the optical axis A-A than against movement parallel to this direction.

In the illustrated advantageous embodiment the illuminating unit 21 comprises a light source 22 and a light diffuser 24 arranged such that light emitted by the light source 22 passes through the light diffuser 24. The illuminating unit 21 is mounted and oriented in such a manner that—in the measurement position illustrated in FIG. 1—the light diffuser 24 is disposed between the prism 14 (and the drop 8) and the light source 22. Like the prism 14, in the measurement condition of the apparatus 4 the illuminating unit 21 is disposed close to the surface 6 of the sample body 7 and is operable to illuminate the drop 8 from a side along or essentially along the surface 6 with light emitted by the light source 22 and diffused by the diffuser 24 for homogenization purposes. In the schematic representation of FIG. 1, the drop 8 is illuminated from the left side, so that a back-lit lighting arrangement is created for the camera 10 and a shadow image of the drop 8 can be recorded by the camera 10, allowing for determining the contour of the drop 8.

The light source 22 may preferably comprise a one- or two-dimensional array of light-emitting elements creating a two-dimensional light field, so that the camera 10 views both the drop 8 and the light field from the side of the drop 8 opposite the light field. The light-emitting elements can be switched on and off selectively for adjusting the width, and possibly also the height, of the light field in order to adapt the light field to the drop or drops 8 at issue. The light diffuser 24 advantageously may be constructed such that it comprises separate diffuser sections for the individual light-emitting elements, which diffuser sections are separated such that each diffuser section receives—and diffuses—light essentially or at least predominantly from the associated light-emitting element only. The light-emitting elements are preferably light-emitting diodes, which may be selected, e.g., from the group consisting of monochromatic light-emitting diodes and white light-emitting diodes. In particular, the light-emitting diodes may be an organic light-emitting diodes or organic light-emitting diodes (OLEDs). Due to their small size, OLEDs may be advantageously in cases in which it is desired to create a light field having a "high resolution", so that the dimension or dimensions can be changed in very small steps and no light diffuser is required.

Figure 2:
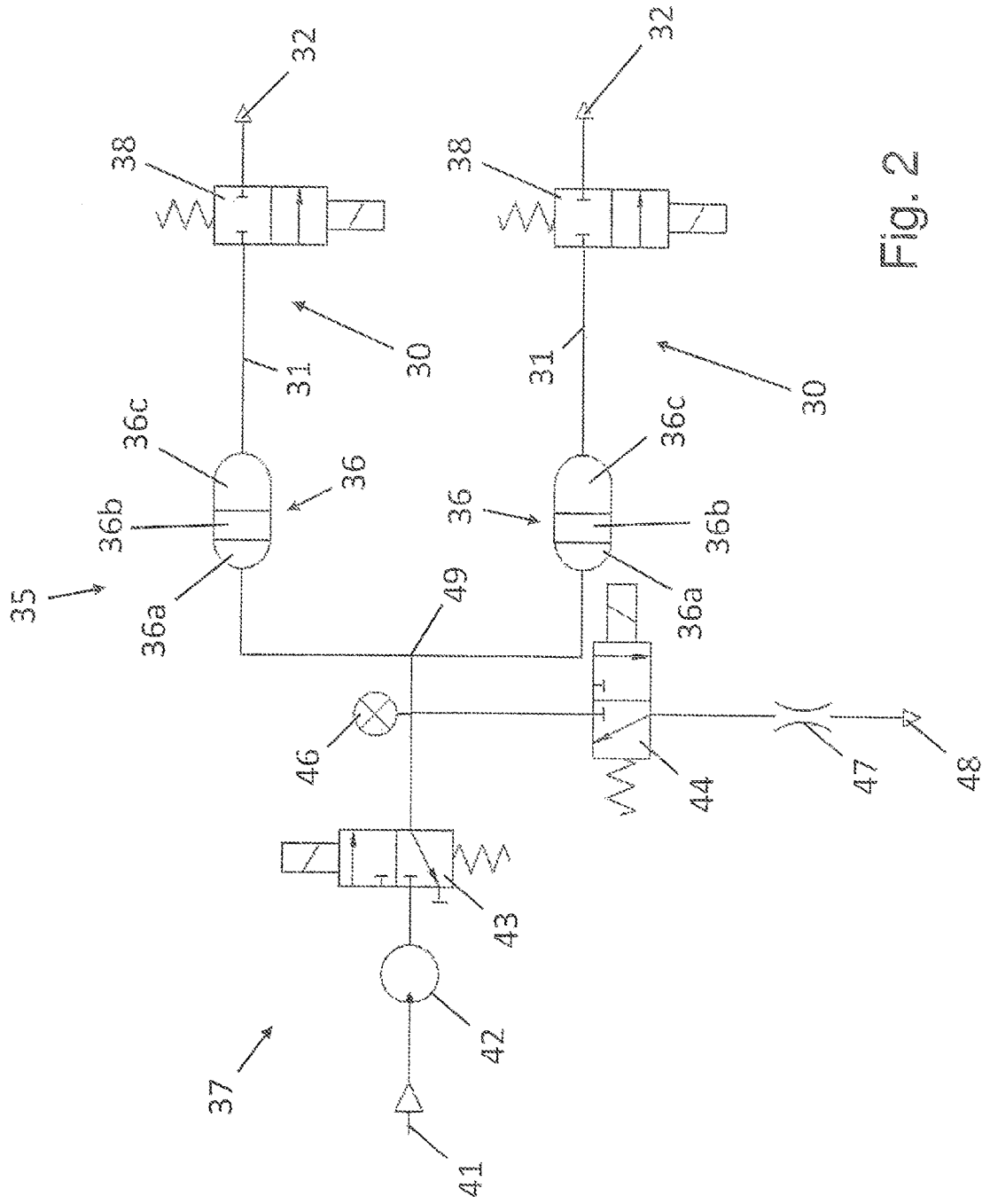
FIG. 2 shows a schematic block diagram of two drop dosing devices used in the contact angle measurement apparatus of FIG. 1.

For applying drops 8 to the surface 6 of the sample body 7, the apparatus 4 further includes two drop dosing devices 30, only one of which is visible in FIG. 1 (the other drop dosing device 30 is located behind the drop dosing device 30 visible in FIG. 1, i.e. behind the plane of the drawing, and can be seen in FIG. 2, and accordingly a drop 8 formed by the other drop dosing device 30 is positioned spaced from the drop 8 visible in FIG. 1 behind the latter drop 8). Each of the drop dosing devices 30 comprises a tube, needle or cannula 31, a nozzle 32 which projects downwardly towards the surface 6 from an opening 33 provided in the bottom side of the housing 5 such that it is spaced from the surface 6, i.e. such that the nozzle 32 projects less from the bottom side of the housing 5 than both the prism 14 and the illuminating unit 21. The nozzle 32 provides an outlet from which liquid transported within the tube or needle 31 can exit to form the drop 8.

At the end 34 of the tube or needle 31 opposite the nozzle 32 the tube or needle 31 is connected to a liquid reservoir arrangement 35. The liquid reservoir arrangement 35 includes two liquid reservoirs 36 in which two different liquids of different polarity are stored, and each tube or needle 31 of the two drop dosing devices 30 is in fluid communication with a different one of the two liquid reservoirs 36, so that the drop dosing devices 30 form drops 8 of the different liquids.

Further, the apparatus 4 comprises within the housing 5 an air system 37 which is operable to provide pressurized air at a defined pressure to the liquid reservoir arrangement 35 and the drop dosing device 30 in order to pressurize the liquids stored in the liquid reservoirs 36 for forcing them under pressure through the tubes or needles 31 and out of the outlets at the nozzles 32 in liquid jets onto the surface 6 to form the drops 8.

The tube or needle 31 of each of the drop dosing devices 30 is normally blocked near the nozzle 32 by a valve 38, which is connected to a controller 39 adapted for controlling opening and closing of the valve 38. Thus, for applying a drop 8 to the surface 6 the controller 39 controls the valve 38 to open for a defined period of time, during which the liquid from the respective liquid reservoir 36 pressurized by the pressurized air is forced by the pressure out of the outlet of the respective nozzle 32, and to then close again, thereby allowing formation of a drop 8, which may advantageously have a defined or essentially defined volume. In an alternative embodiment the nozzle 32 and the valve 38 of each of the drop dosing devices 30 may be provided as a single component, i.e. as a nozzle having an integrated valve.

The controller 39 is also connected to each of the illuminating device 20, the liquid reservoir arrangement 35 and the air system 37 for controlling operation of these components, and to a processing device 40 operably connected to the camera 10. The processing device 40 in turn controls operation of the camera 10 and is adapted and operable to receive and analyze images recorded by the camera 10.

In the illustrated embodiment both the controller 39 and the processing device 40 are shown as being disposed inside the housing 5. For example, the controller 39 may be provided as a microcontroller. However, it is also possible that the controller 39 and/or the processing device 40 is provided as a separate device outside the housing 5, for example as a suitably programmed computer or PC.

The air system 37, the liquid reservoir arrangement 35 and the two drop dosing devices 30 are shown in more detail in the schematic block diagram of FIG. 2.

As can be seen in FIG. 2, the air system 37 comprises an air inlet 41, a pump 42 pressurizing air received through the air inlet 41, two valves 43 and 44, a pressure sensor 46 located and operable to sense the pressure of the pressurized air, a throttle valve 47, a pressure relief outlet 48, and an outlet 49 coupled in fluid communication to the liquid reservoir arrangement 35 for providing pressurized air to the liquid reservoirs 36. The controller 39 is adapted to function, amongst others, as a pressure regulator, which is operable to regulate the pressure of the pressurized air. Adjustment of the pressure of the pressurized air towards higher values can involve suitably adjusting operation of the pump 42, and adjustment of the pressure of the pressurized air towards lower values can be effected by suitably opening the valve 44 in order to relief pressure through the throttle valve 47 and the pressure relief outlet 48, wherein the throttle valve 47 limits maximum flow. For this purpose, the sensor 46, the valve 44, and the pump 42 (and possibly also the valve 43) are connected to the controller 39 such that the pressure regulator implemented by the controller 39 receives sensor signals from the sensor 46 and is able to control operation of the valve 44, and the pump 42 (and possibly also the valve 43) based on the sensed pressure in order to adjust the pressure at the outlet 49 to the defined pressure. The valve 43 is provided for avoiding an undesired pressure drop upon switching off the pump 42.

In FIG. 2 it is further shown that the pressurized air is provided through the outlet 49 to an air reservoir portion 36a of each of the two liquid reservoirs 36, each of which air reservoir portion 36a is separated from a liquid reservoir portion 36c, in which the liquid is actually stored, by a gas-liquid separator 36b. In this manner, the liquids stored in the liquid reservoir portions 36c are pressurized by the pressurized air, thereby driving them out of the liquid reservoir portions 36c, through the tubes or needles 31 and out of the outlets at the nozzles 32 upon opening the valves 38.

For carrying out a contact angle and surface free energy measurement with two drops 8, an operator positions the apparatus 4 above the surface 6 of the sample body 7 in the position illustrated in FIG. 1 and presses a button 50 mounted on the housing 5 and connected to the controller 39. The controller 39 is adapted to detect pressing of the button 50 and to then initiate an automatic control sequence, in which—possibly following control or adjustment of the pressure of the pressurized air by checking the pressure sensed by the pressure sensor 46 and operating the pressure regulator in the manner described above—the valves 38 are opened, e.g. simultaneously, for a defined period of time in order to apply the liquids in jets to the surface 6 to form two drops 8 next to each other, and to then close the valves 38 again. Then, the illuminating device 20 is controlled to illuminate the drops 8 from the left-hand side in FIG. 1, and the camera 10 is operated—via the processing device 40 or alternatively via the controller 39—to record a shadow image of both drops 8 viewing them from the right-hand side in FIG. 1. The processing device 40 receives the image and carries out a contour analysis for both drops 8 and subsequently a determination of the contact angle for each drop 8. Further, the processing device 40 may be adapted to determine the surface free energy from the two contact angles. Thus, the measurement is carried out automatically in a very simple manner by simply pressing the button 50.

Importantly, the controller 39 is adapted to adjust the defined pressure of the pressurized air and/or the degree of opening of the valve 38 in such a manner that for each drop dosing device 30 the liquid is applied to the surface in the jet 51 with a flow rate of 45 µl/s or less, preferably about 40 µl/s or less, more preferably about 35 µl/s or less, even more preferably about 30 µl/s or less, and most preferably 25 µl/s or about 25 µl/s.

Further, for each drop dosing device 30 the nozzle 32 is preferably configured such that the diameter of the jet of liquid exiting the outlet at the nozzle 32 does not exceed a specific value depending on the diameter of the drop 8 to be formed. FIG. 3 schematically illustrates a drop 8 on the surface 6 during formation of the drop 8 as viewed by the camera 10. Since most surfaces have some reflecting properties, a reflection 8' of the drop 8 can be seen in the Figure. Also depicted is the jet 51 of liquid originating from the tip 32. As can be seen, the diameter $D_j$ of the jet 51 is much smaller than the diameter $D_d$ of the drop 8, and for a drop 8 having a contact angle of 90° the ratio $D_j/D_d$ is preferably 0.2 or smaller. In case different drop sizes shall be possible, the nozzles 32 may be configured such that, under control of the controller 39, they can be opened with variable flow cross-sections in order to change the jet diameter. Thus, adjustable nozzles 32 may be provided.

Instead of the air system, the apparatus 4 generally may also comprise a compressed gas system using a gas different than air, such as, e.g., $CO_2$. Such a compressed gas system is constructed and operating identically to the air system described above, with the only difference being that a gas other than air is used. No other change to the described apparatus 4 is necessary.

The invention claimed is:

1. A contact angle measurement apparatus for measuring a contact angle between a surface of a solid sample body and at least one drop of sample liquid disposed on the surface, the apparatus comprising:
   a liquid reservoir arrangement for storing at least one liquid,
   at least one drop dosing device in fluid communication with the liquid reservoir arrangement and adapted and arranged for applying a drop of a liquid stored in the liquid reservoir arrangement onto a surface of a sample body,
   an illuminating device adapted and arranged for illuminating each drop applied by the at least one drop dosing device and disposed on the surface from a first side of the at least one drop, and
   an image recording device adapted and arranged for recording an image of at least a transition region between the surface and each drop applied by the at least one drop dosing device and disposed on the surface in side view from a second side of the drop opposite the first side,
   characterized in that
   each of the at least one drop dosing device comprises a liquid line, which comprises an outlet and a valve adapted for selectively blocking and allowing flow of liquid through the liquid line, and which is adapted to guide a liquid stored in the liquid reservoir arrangement towards the outlet and out of the outlet onto the surface, and
   the contact angle measurement apparatus further comprises:
   a liquid pressurizing system which is adapted to pressurize liquid from the liquid reservoir arrangement, and
   a controller connected to the valve of each of the at least one drop dosing device and to the liquid pressurizing system and adapted to control operation of the liquid pressurizing system and, for each of the at least one drop dosing device, opening and closing of the respective valve to apply a drop of the respective liquid from the respective liquid line to the surface in a jet of pressurized liquid, wherein for each of the at least one drop dosing device the controller and the valve are adapted such that the jet applies the liquid to the surface as a continuous stream with a flow rate of 45 μl/s or less.

2. The contact angle measurement apparatus according to claim 1, wherein for each of the at least one drop dosing device the liquid line and the valve are configured such that, when applying a drop having a contact angle of 90°, the ratio of the diameter of the jet to the diameter of the drop is 0.2 or less.

3. The contact angle measurement apparatus according to claim 1, wherein the controller is adapted to adjust, for each of the at least one drop dosing device, the drop volume by adjusting the time interval during which the respective valve is opened, the degree of opening of the respective valve and/or the pressure to which the respective liquid is pressurized by the liquid pressurizing system.

4. The contact angle measurement apparatus according to claim 1, wherein the liquid pressurizing system includes a compressed gas system, which comprises a source of pressurized gas adapted to provide pressurized gas at a defined pressure and which is adapted to pressurize liquid from the liquid reservoir arrangement using the pressurized gas.

5. The contact angle measurement apparatus according to claim 4, wherein the source of pressurized gas comprises:
   a pump adapted for pressurizing gas,
   a pressure regulator adapted to regulate the pressure of gas pressurized by the pump,
   a pressure sensor connected to the pressure regulator and adapted to sense the pressure of the pressurized gas regulated by the pressure regulator and to provide a corresponding sensing signal to the pressure regulator enabling the pressure regulator to determine the sensed pressure, and
   a pressure relief valve connected to the pressure regulator and adapted to selectively relief pressurized gas,
   wherein the pressure regulator is adapted to control the pump and the pressure relief valve to automatically adjust the pressure of the pressurized gas based on the pressure sensed by the pressure sensor and a defined pressure in order to provide the pressurized gas with the defined pressure.

6. The contact angle measurement apparatus according to claim 1, wherein each of the at least one drop dosing device is arranged to apply drops of liquid in a field of view of the image recording device and/or in a region illuminated by the illuminating device.

7. The contact angle measurement apparatus according to claim 1, wherein the at least one drop dosing device, the illuminating device and the image recording device are integrated into a movable measurement head.

8. The contact angle measurement apparatus according to claim 1, further comprising a processing device adapted for carrying out a contour recognition of any drops present in images recorded by the image recording device and determining for each of these drops a contact angle from the recognized contour.

9. The contact angle measurement apparatus according to claim 1, comprising two of the drop dosing devices, wherein the outlets of the two drop dosing devices are arranged such that two drops can be applied to the surface next to each other.

10. The contact angle measurement apparatus according to claim 9, wherein the liquid reservoir arrangement comprises two liquid reservoirs for storing two different liquids, and wherein the liquid line of each of the two drop dosing devices is in fluid communication with a different one of the two liquid reservoirs.

11. The contact angle measurement apparatus according to claim 9, wherein the controller is adapted to control the valves of the two drop dosing devices in such a manner that the two drop dosing devices apply two drops to the surface next to each other simultaneously or successively.

12. The contact angle measurement apparatus according to claim 9, wherein the image recording device is adapted to record an image of the two drops simultaneously.

13. The contact angle measurement apparatus according to claim 1, further comprising an actuation means for actuation by an operator and connected to the controller, wherein the controller is adapted to detect actuation of the actuation means and, upon detecting actuation, to automatically control the at least one drop dosing device to apply a respective drop of liquid to the surface, the illuminating device to illuminate each drop applied by the at least one drop dosing device, and the image recording device to record an image of each of the drops illuminated by the illuminating device.

14. The contact angle measurement apparatus according to claim 13, wherein the controller is adapted to automatically control, upon detecting actuation of the actuation means, each of the two drop dosing devices such that two drops are applied to the surface next to each other.

15. A method for measuring a contact angle between a surface of a solid sample body and at least one drop of sample liquid disposed on the surface with a contact angle measurement apparatus, the apparatus comprising:
   a liquid reservoir arrangement,
   at least one drop dosing device in fluid communication with the liquid reservoir arrangement and comprising a liquid line, which comprises an outlet and a valve adapted for selectively blocking and allowing flow of liquid through the liquid line, and which is adapted to guide a liquid stored in the liquid reservoir arrangement towards the outlet and out of the outlet onto the surface,
   an illuminating device,
   an image recording device,
   a liquid pressurizing system, and
   a controller connected to the valve of each of the at least one drop dosing device and to the liquid pressurizing system, the method comprising the following steps:
      storing at least one liquid in the liquid reservoir arrangement,
      pressurizing liquid from the liquid reservoir arrangement with a liquid pressurizing system,
      applying a drop of the at least one liquid stored in the liquid reservoir arrangement onto the surface of the sample body with the at least one drop dosing device in a jet of pressurized liquid by opening and closing of the respective valve with the controller, wherein the jet applies the liquid to the surface as a continuous stream with a flow rate of 45 µl/s or less,
      illuminating the drop disposed on the surface from a first side of the drop with the illuminating device, and
      recording an image of at least a transition region between the surface and the drop disposed on the surface in side view from a second side of the drop opposite the first side.

* * * * *